United States Patent [19]

Hoelderich et al.

[11] Patent Number: 4,560,822

[45] Date of Patent: Dec. 24, 1985

[54] PREPARATION OF DIENES BY DEHYDRATION OF ALDEHYDES

[75] Inventors: Wolfgang Hoelderich; Franz Merger; Wolf D. Mross, all of Frankenthal; Gerd Fouquet, Neustadt, all of Fed. Rep. of Germany

[73] Assignee: BASF Aktiengesellschaft, Ludwigshafen, Fed. Rep. of Germany

[21] Appl. No.: 730,687

[22] Filed: May 3, 1985

[30] Foreign Application Priority Data

May 24, 1984 [DE] Fed. Rep. of Germany ....... 3419379

[51] Int. Cl.$^4$ .............................................. C07C 1/24
[52] U.S. Cl. ..................................................... 585/606
[58] Field of Search ...................... 585/606, 601, 603

[56] References Cited

U.S. PATENT DOCUMENTS 2,421,361 11/1946 Toussaint et al. ................... 585/606
2,421,762 12/1946 Workman ............................. 585/606

FOREIGN PATENT DOCUMENTS 2163396 6/1973 Fed. Rep. of Germany ...... 585/606
1385348 2/1975 United Kingdom ............... 585/606
2063297 1/1981 United Kingdom ............... 585/606
2093060 8/1982 United Kingdom ............... 585/606

Primary Examiner—D. E. Gantz
Assistant Examiner—A. Pal
Attorney, Agent, or Firm—John H. Shurtleff

[57] ABSTRACT

Dienes are prepared by dehydration of aldehydes at elevated temperatures by a method in which the dehydration is carried out using a zeolite as a catalyst.

7 Claims, No Drawings

PREPARATION OF DIENES BY DEHYDRATION OF ALDEHYDES

The present invention relates to a process for the preparation of dienes by dehydration of aldehydes using zeolites as catalysts.

Because of their versatility, dienes are desirable chemical compounds. They are required, for example, in the rubber and plastics industries and as starting materials and intermediates in a large variety of organic reactions. The preparation of dienes from aldehydes by simple dehydration is desirable since the aldehydes are readily obtainable, for example via the oxosynthesis. The preparation is carried out, for example, over a phosphorus-containing catalyst, examples of catalysts used being acids, such as phosphoric acid (German Laid-Open Application DOS No. 2,163,396), boron phosphates (European Pat. No. 80,449) and ammonium aluminum sulfates (British Pat. No. 2,063,297). In these methods, the dilution with steam is a disadvantage. Moreover, the catalysts deactivated by coking can be regenerated only with difficulty if at all.

We have found that, in the catalytic dehydration of aldehydes to dienes at elevated temperatures, particularly advantageous result are obtained if the dehydration is carried out using zeolites as catalysts.

In the novel process, high selectivities and conversions are obtained and the catalyst has a long life. Other advantages are that high selectivities coupled with a long catalyst life are obtained even in the absence of steam, and that the catalysts used according to the invention can easily be regenerated with air after they have been deactivated by coking.

Aldehydes which can be dehydrated by the novel process to give dienes are, for example, those of the formula

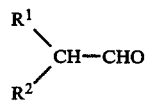

In formula I, $R^1$ and $R^2$ are identical or different, $R^1$ is alkyl with 1 to 3 carbon atoms or hydrogen and $R^2$ is alkyl with 1 to 8 carbon atom or a hydrocarbon radical which together with $R^1$ forms a cyclohexyl radical.

Particularly suitable aldehydes of the stated type are those which carry a hydrogen atom at an alpha carbon atom. Examples of aldehydes are butanal, 2-methylbutanal, 2-methylpentanal, 2-ethylhexanal, pivalaldehyde, 2-benzylpropanal, 2-ethylbutanal, cyclohexanecarbaldehyde and isovaleraldehyde. The starting compounds can be prepared, for example, from olefins by the oxosynthesis. For example, 2-methylbutanal is obtained by hydroformylation of but-2-ene.

Zeolites are used as catalysts for the novel dehydration of the aldehydes to the dienes. Zeolites are crystalline aluminosilicates which possess a highly ordered structure with a rigid three-dimensional network of $SiO_4$ and $AlO_4$ tetrahedra which are connected through common oxygen atoms. The ratio of Si and Al atoms to oxygen is 1:2. The electrovalency of the aluminum-containing tetrahedra is compensated by inclusion of cations in the crystal, e.g. an alkali metal or hydrogen ion. Cation exchange is possible. The spaces between the tetrahedra are occupied by water molecules prior to dehydration by drying or calcination. The zeolite can also contain trivalent elements such as B, Ga, Fe or Cr instead of the aluminum, and tetravalent elements such as Ge instead of the silicon.

Preferably used catalyst are zeolites of the pentasil type, which can have different chemical compositions, these are aluminosilicate, borosilicate, iron silicate, gallium silicate, chromium silicate, arenosilicate and bismuth silicate zeolites or mixtures of these, and aluminogermanate, borogermanate, gallium germanate and iron germanate zeolites and mixtures of these. Aluminosilicate, borosilicate and iron silicate zeolites of the pentasil type are particularly preferrred.

The aluminosilicate zeolite is prepared, for example, from an aluminum compound, preferably $Al(OH)_3$ or $Al_2(SO_4)_3$, and a silicon component, preferably highly disperse silicon dioxide, in aqueous amine solution, in particular 1,6-hexanediamine, 1,3-propanediamine or triethylenetetramine solution, with or without the addition of an alkali metal or alkaline earth metal, at from 100° to 220° C., under autogenous pressure. The resulting aluminosilicate zeolites have an $SiO_2/Al_2O_3$ ratio of from 10 to 40,000, depending on the amounts of starting materials chosen. The aluminosilicate zeolite can also be prepared in an ether medium, such as diethylene glycol dimethyl ether, in an alcohol medium, such as methanol or butane-1,4-diol, or in water.

The borosilicate zeolite is synthesized, for example, at from 90° to 200° C. under autogenous pressure, by reacting a boron compound, e.g. $H_3BO_3$, with a silicon compound, preferably highly dispere silicon dioxide, in an aqueous amine solutiom, in particullar 1,6-hexanediamine, 1,3-propanediamine or triethylenetetramine solution, with or without the addition of an alkali metal or alkaline earth metal. In this reaction, the aqueous amine solution may be replaced with a solution of an amine in an ether, e.g. diethylene glycol dimethyl ether, or with an alcoholic solution, e.g. in hexane-1,6-diol, as the solvent.

The iron silicate zeolite is obtained, for example, from an iron compound, preferably $Fe_2(SO_4)_3$, and a silicon compound, preferably highly disperse silicon dioxide, in an aqueous amine solution, in particular 1,6-hexanediamine with or without the addition of an alkali metal or alkaline earth metal, at from 100° to 200° C., under autogenous pressure.

The aluminosilicate, borosilicate and iron silicate zeolites prepared in this manner are isolated, dried at from 100° to 160° C., preferably 110° C., and calcined at from 450° to 550° C., preferably 500° C., after which they can be molded with a binder in a weight ratio of from 90:10 to 40:60 to give extrudates or tablets. Suitable binders include a variety of aluminas, preferably boehmite, amorphous aluminosilicates having an $SiO_2/Al_2O_3$ ratio of from 25:75 to 95:5, preferably 75:25, silicon dioxide, preferably highly disperse $SiO_2$, mixtures of highly disperse $SiO_2$ and highly disperse $Al_2O_3$, highly disperse $TiO_2$ and clay. After the molding procedure, the extrudates or tablets are dried for 16 hours at 110° C. and calcined for 16 hours at 500° C. Such catalysts can be particularly advantageously prepared by molding the isolated aluminosilicate, borosilicate or iron silicate zeolite directly after drying, and subjecting it to calcination only after the molding procedure. Flluidizable material having a size of from 0.1 to 0.5 mm can be obtained from the extruded catalyst by milling and screening. The aluminosilicate, borosilicate and iron silicate zeolites can, however, also be used in pure form as extrudates or tablets, without binder.

Aluminosilicate zeolites of the Y type which are prepared from silica sol (29% of $SiO_2$) and sodium aluminate in aqueous medium can also be used as catalysts. These aluminosilicate zeolites can also be molded with binders before being used. Zeolites of the mordenite type may also be used.

If, because of the method of preparation, the zeolite is not present in the acidic H form preferred for catalysis but, for example, in the Na form, it can be partially or completely converted to the desired H form by ion exchange with ammonium ions followed by calcination, or by treatment with an acid. The zeolites may furthermore be modified in a variety of ways in order to increase the selectivity, the catalyst life and the number of possible regenerations. In a suitable method of modification, for example, the unmolded or molded zeolite can be impregnated, or subjected to ion exchange, with alkali metals such as Na (provided the alkali metal form of the zeolite is not already obtained in the synthesis), with alkaline earth metals, such as Ca or Mg, or with earth metals, such as B or Tl. Doping of the zeolites with transition metals, such as Mo, W, Fe, Zn or Cu, with noble metals, such as Pd and with rare earth metals, such as Ce or La, is particularly advantageous.

In practice, such modified catalysts are produced, for example, as follows: the molded pentasil zeolite is initially taken in a siphon tube, and, for example, an aqueous solution of a halide or of a nitrate of one of the above metals is passed over at from 20° to 100° C. This type of ion exchange can be carried out, for example, over the hydrogen, ammonium or alkali metal form of the zeolite. The metal can also be applied to the zeolite by, for example, impregnating the zeolite material with a halide, a nitrate or an oxide of the above metals in an aqueous or alcoholic solution. Both ion exchange and impregnation are followed by one or more drying procedures, and, if desired, further calcination.

The specific procedure is, for example, as follos: molybdenum oxide ($MoO_3$), tungstic acid ($H_2WO_4$) or $Ce(NO_3)_3.6H_2O$ is dissolved in water, or the major part of it is dissolved. This solution is then used to impregnate the extruded or unextruded zeolite for a certain time (about 30 minutes). The supernatant solution is freed from water in a rotary evaporator, after which the impregnated zeolite is dried at about 150° C. and calcined at about 550° C. This impregnation process can be carried out several times in succession in order to obtain the desired metal content.

It is also possible, for example, to prepare an ammoniacal $Pd(NO_3)_2$ solution, and to suspend the pure zeolite powder therein for about 24 hours at from 40 to 100° C., while stirring. After filtration, drying at about 150° C. and calcination at about 500° C., the zeolite material thus obtained can be further processed, with or without a binder, to give extrudates, pellets or fluidizable material.

Ion exchange with the zeolite in the H form can be carried out by initially introducing the zeolite in the form of extrudates or pellets into a column, and circulating over it, for example, an ammoniacal $Pd(NO_3)_2$ solution at slightly elevated temperatures of from 30 to 80° C. for from 15 to 20 hours. This is followed by washing thoroughly with water, drying at about 150° C. and calcining at about 550° C.

For some metal-doped zeolites, after-treatment with hydrogen is advantageous.

In another possible method of modification, the zeolite material, in molded or unmolded form, is subjected to a treatment with an acid, such as hydrochloric acid, hydrofluoric acid or phosphoric acid and/or with steam. In an advantageous procedure, for example, the zeolite powder, before being molded, is treated with from 0.001 to 2 N, preferably from 0.05 to 0.5 N, hydrofluoric acid under reflux for from 1 to 3 hours. The product is filtered off and washed thoroughly, after which it is dried at from 100° to 160° C. and calcined at from 400° to 550° C. It may also be advantageous to treat the zeolites with hydrochloric acid after they have been molded with the binder. In this procedure, the zeolite is treated with, for example, from 3 to 25, in particular from 12 to 20, % strength hydrochloric acid at from 60° to 80° C. for from 1 to 3 hours, and then washed thoroughly, dried at from 100° to 160° C. and calcined at from 400° to 550° C. The zeolite may also be modified by applying phosphorus compounds, such as trimethoxyphoshpate.

When the zeolite catalysts have become deactivated, which may occur as a result of coking during the process of the invention, they can be regenerated in a simple manner by burning off the coke deposit with air or with an air/$N_2$ mixture at from 400° to 550° C., preferably 500° C., with the result that they again attain their initial activity. The activity of the catalyst can furthermore be set to achieve optimum selectivity of the desired product by partial coking (pre-coke). If the dehydration is carried out in the presence of gases such as hydrogen, nitrogen and steam, the product composition and the life of the catalyst can be influenced by these. In general, the catalysts are used alternatively as 2–4 mm extrudates, as tablets having a diameter of from 3 to 5 mm, or as a powder having particle sizes of from 0.3 to 0.5 mm or (as a fluidizable catalyst) from 0.1 to 0.5 mm.

The dehydration of the aldehydes to the dienes is carried out over the zeolites preferably at from 150° to 600° C., in particular from 300° to 500° C. The space velocity (WHSV) is from 0.1 to 20, preferably from 0.5 to 5, g of aldehyde per g of catalyst per hour. The dehydration may also be carried out in the liquid phase, for example at from 30° to 300° C. The process can be effected by a batchwise or continuous method, under atmospheric or superatmospheric pressure, for example in a continuous-flow reactor, a stirred kettel or a fluidizedbed reactor. Unconverted aldehydes can, if required, be separated off from the resulting dienes by distillation after reaction, and can be reused for the reaction according to the invention.

EXAMPLE 1 to 5

The aldehydes below were dehydrated to the corresponding dienes:
1. 2-methylbutanal to isoprene
2. 2-methylpentanal to 2-methylpenta-1,3-diene
3. pivalaldehyde to isoprene
4. isovaleraldehyde to isoprene
5. cyclohexanecarbaldehyde to methylcyclohexadiene and/or methylenecyclohexene.

The reactions were carried out as described below.

To dehydrate it to the diene, the particular aldehyde was introduced into a tube reactor (spiral form, internal diameter 0.6 cm, length 90 cm) under isothermal conditions, and passed over a zeolite catalyst at from 350° to 450° C., in the gas phase. The reaction products obtained ere worked up by distillation and characterized by their boiling points, refractive indices and NMR spectra. Quantitative determination of the products and of the starting materials was carried out by gas chromatography. The type of catalyst, the temperature, the space velocity (WHSV), the conversion and the selectivity are shown in the Table below. The effect of the temperature on the conversion and the selectivity is described in Example 5.

was obtained. The zeolite was molded with boehmite in a weight ratio of 60:40 to give 2 mm extrudates, which were dried at 110° C. for 16 hours and calcined at 500° C. for 24 hours. 50 g of these extrudates were impregnated for 1 hour with 16.5 g of trimethoxyphosphate dissolved in 35 g of water, after which the catalyst was dried at 110° C. for 2 hours. Its phosphorus content was

| Example | 1 | 1 | 2 | 3 | 4 | 5 | 5 | 5 |
|---|---|---|---|---|---|---|---|---|
| Catalyst | A | C | A | A | A | A | A | A |
| Temperature °C. | 400 | 400 | 350 | 450 | 500 | 350 | 400 | 450 |
| WHSV | $2\,h^{-1}$ | $2\,h^{-1}$ | $2\,h^{-1}$ | $1.8\,h^{-1}$ | $2\,h^{-1}$ | $2\,h^{-1}$ | $2\,h^{-1}$ | $2\,h^{-1}$ |
| Conversion % | 51.2 | 49.0 | 21.0 | 99.6 | 50.7 | 63.9 | 85.9 | 95.5 |
| Selectivity Diene % | 95.0 | 83.6 | 91.5 | 50 | 85.5 | 90.8 | 95.6 | 89.6 |

The catalysts used were prepared as described below:

Catalyst A

The catalyst was prepared by a hydrothermal synthesis from 64 g of $SiO_2$ (highly disperse silica), 12.2 g of $H_3BO_3$ and 800 g of aqueous hexanediamine solution (50:50 (w/w) mixture) at 170° C. under autogenous pressure in a stirred autoclave. The crystalline product was filtered off, washed thoroughly, dried at 100° C. for 24 hours and calcined at 500° C. for 24 hours. The product obtained was a borosilicate zeolite of the pentasil type which contained 92.4% by weight of $SiO_2$ and 2.32% by weight of $B_2O_3$. This zeolite was converted to 2 mm extrudates, which were dried at 100° C. and calcined for 24 hours at 500° C.

Catalyst B

An aluminosilicate zeolite of the pentasil type was prepared under hydrothermal conditions, under atuogenous pressure and at 150° C., from 65 g of highly disperse $SiO_2$ and 20.3 g of $Al_2(SO_4)_3.18H_2O$ in 1 kg of an aqueous 1,6-hexanediamine solution (50:50 (w/w) mixture) in a stirred autoclave. The crystalline product was filtered off, washed thoroughly, dried at 110° C. for 24 hours and calcined at 500° C. for 24 hours. This aluminosilicate zeolite contained 91.6% by weight of $SiO_2$ and 4.6% by weight of $Al_2O_3$.

50 g of this product were refluxed with 140 ml of 0.1 N HF for 1 hour. The product as filtered off, washed neutral with water, dried at 110° C. for 16 hours and calcined at 500° C. for 5 hours. This zeolite was molded with an amorphous aluminosilicate (75% by weight of $SiO_2$ and 25% by weight of $Al_2O_3$) in a weight ratio of 60:40 to give 2 mm extrudates, and the latter were dried at 110° C. for 16 hours and calcined at 500° C. for 24 hours.

Catalyst C

The procedure described for catalyst B was followed, except that the 1,6-hexanediamine was replaced by 1,3-propanediamine. An aluminosilicate zeolite containing 90.6% by weight of $SiO_2$ and 3.4% by weight of $Al_2O_3$ 1.5% by weight.

We claim:

1. A process for the preparation of a diene, wherein an aldehyde of the formula

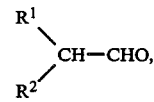

where $R^1$ and $R^2$ are identical or different, $R^1$ is alkyl with 1 to 3 carbon atoms or hydrogen and $R^2$ is alkyl with 1 to 8 carbon atoms or a hydrocarbon radical which together with $R^1$ forms a cyclohexyl radical, is converted at from 150° to 600° C. over a zeolite as a catalyst.

2. A process for the preparation of a diene of the formula

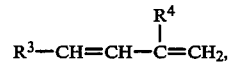

where $R^3$ is methyl, ethyl or hydrogen and $R^4$ is methyl or ethyl, wherein 2-methylbutanal, 2-methylpentanal, 2-ethylhexanal, 3-methylbutanal, isovaleraldehyde or pivalaldehyde is passed at from 300° to 500° C. over a zeolite as a catalyst.

3. A process for the preparation of methylcyclohexadiene, wherein cyclohexanecarbaldehyde is passed at from 300° to 500° C. over a zeolite as a catalyst.

4. A process as claimed in claim 1, wherein a zeolite of the pentasil type is used.

5. A process as claimed in claim 1, wherein an aluminosilicate zeolite is used

6. A process as claimed in claim 1, wherein a borosilicate zeolite is used.

7. A process as claimed in claim 1, wherein an iron silicate zeolite is used.

* * * * *